United States Patent [19]

Noble

[11] Patent Number: 4,753,739
[45] Date of Patent: Jun. 28, 1988

[54] BLOOD BAG SUPPORT SYSTEM

[75] Inventor: Bradley T. Noble, Greeley, Colo.

[73] Assignee: Engineering & Research Associates, Tucson, Ariz.

[21] Appl. No.: 822,381

[22] Filed: Jan. 27, 1986

[51] Int. Cl.$^4$ .................... B01D 21/26; B04B 15/00
[52] U.S. Cl. ..................... 210/787; 210/513; 210/512.1; 494/20; 494/21; 494/37; 494/45
[58] Field of Search .............. 494/20, 16, 21, 45, 494/37; 222/95, 103; 210/782, 787, 360.1, 361, 789, 927, 513, 514, 512.1

[56] References Cited

U.S. PATENT DOCUMENTS

| Re. 25,129 | 2/1962 | Walter | 604/252 |
|---|---|---|---|
| 3,559,880 | 2/1971 | Naito et al. | 494/21 |
| 3,672,564 | 6/1972 | Schlutz et al. | 494/17 |
| 3,674,197 | 7/1972 | Mitchell et al. | 494/17 |
| 3,830,425 | 8/1974 | Stallmann | 494/45 |
| 4,146,172 | 3/1979 | Cullis et al. | 210/927 X |
| 4,213,561 | 7/1980 | Bayham | 494/21 |
| 4,266,717 | 5/1981 | Jennings et al. | 210/927 X |
| 4,284,209 | 8/1981 | Barbour, Jr. | 222/103 X |
| 4,439,177 | 3/1984 | Conway | 494/20 |
| 4,543,084 | 9/1985 | Bailey | 494/20 |

FOREIGN PATENT DOCUMENTS 11854   1/1983   Japan ................. 210/927

Primary Examiner—Peter Hruskoci
Assistant Examiner—W. Gary Jones
Attorney, Agent, or Firm—Cahill, Sutton & Thomas

[57] ABSTRACT

A blood bag support system is described which is very useful for supporting a blood bag in a centrifuge. The support system includes two upright support members and horizontal connecting means extending between the upright supports. A blood bag is suspended from the connecting means. The support system is balanced so as to avoid vortexing or mixing inside the blood bag during centrifuging. The support system holds up the ports at the top of the bag, enabling red blood cells in the ports to be forced downwardly during centrifuging. This prevents contamination of blood components with red blood cells.

10 Claims, 2 Drawing Sheets

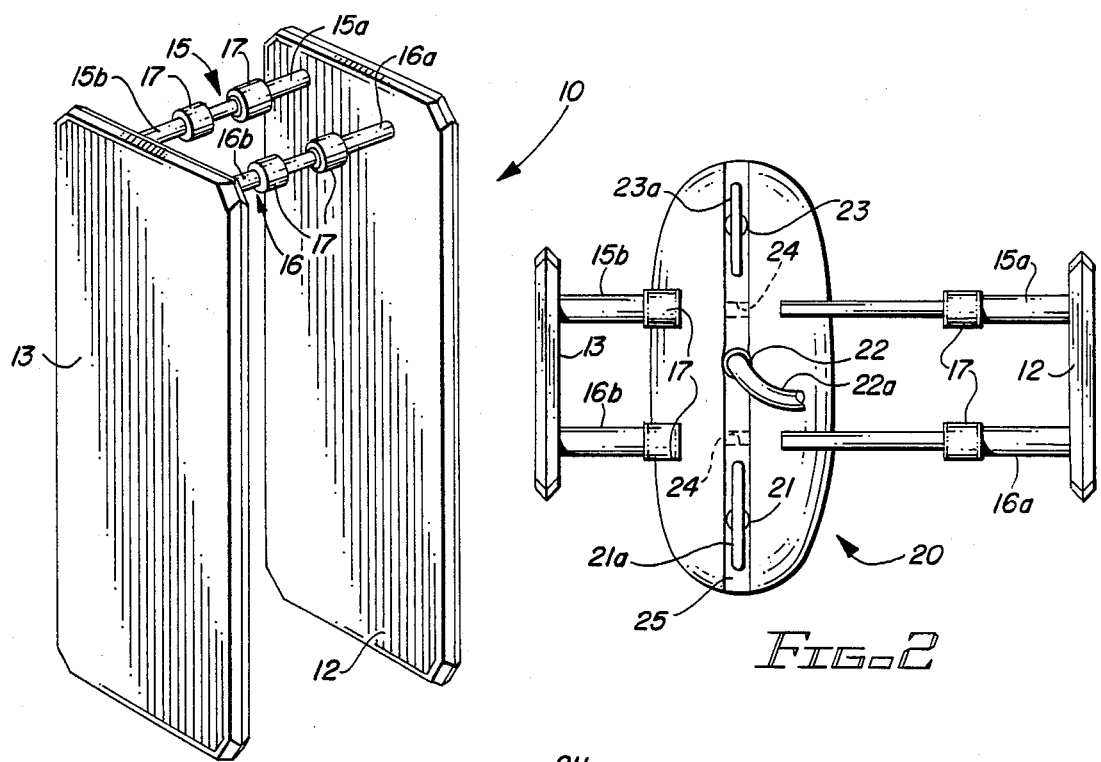
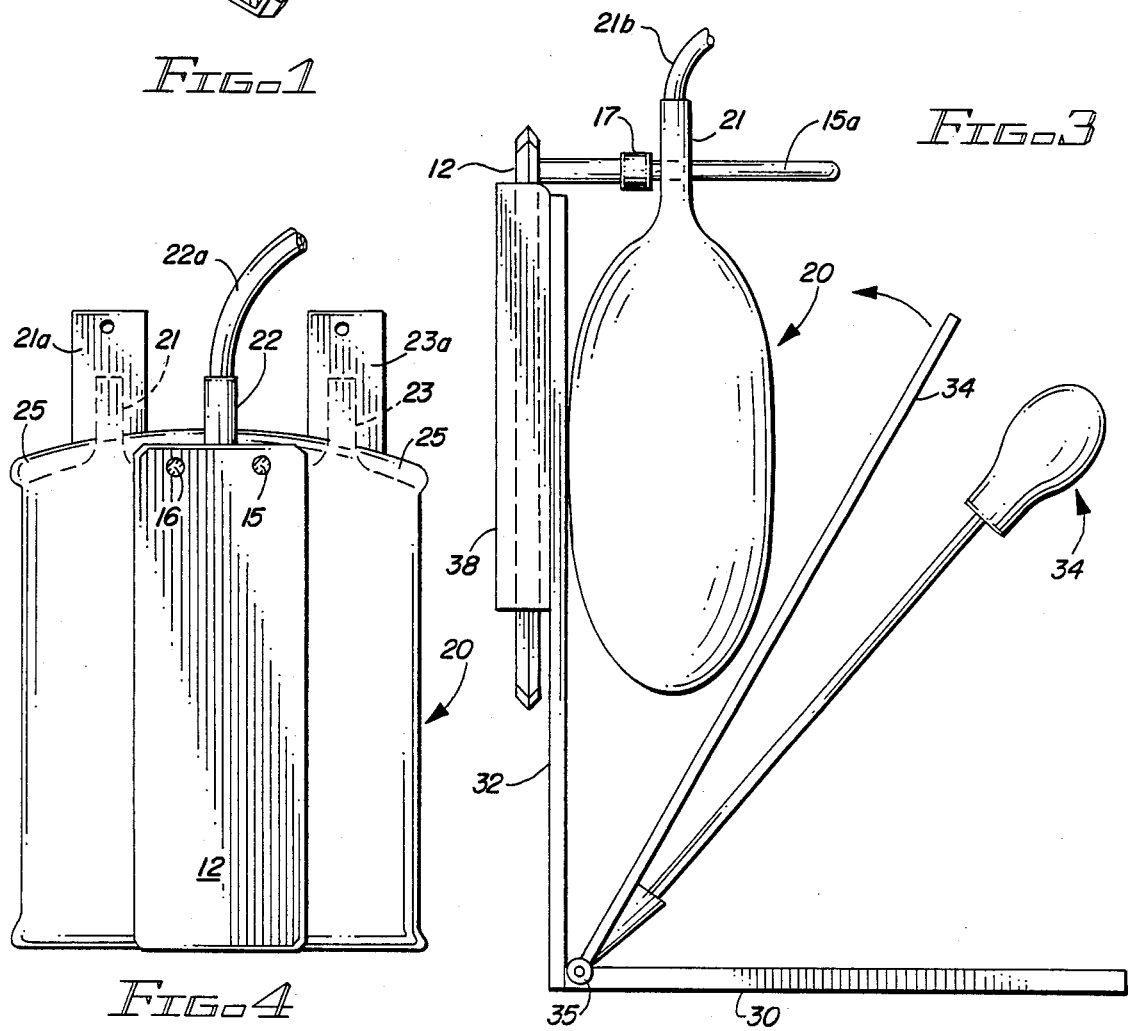

BLOOD BAG SUPPORT SYSTEM

FIELD OF THE INVENTION

This invention relates to support systems for blood bags during centrifuging to separate plasma from red blood cells in whole blood. This invention also relates to support systems for supporting blood bags after centrifuging when the plasma is expressed or extracted from the blood bags.

BACKGROUND OF THE INVENTION

The use of plastic bags to contain blood has been common for many years. Blood is also centrifuged in such bags to separate plasma, red blood cells, and white blood cells. Plasma is the non-cellular component of blood. Useful plasma for medical purposes must be platelet-rich and void of red blood cells and white blood cells.

Plastic bags used for this purpose typically comprise two sheets of heavy plastic which have been sealed together at their edges. At the top edge of the bag there is a flap formed by the two sheets being sealed together. Typically there is a port or opening at the top of the bag which communicates with the interior cavity of the bag. The port normally appears as a cylindrical, tubular member to which an elongated flexible tube is normally attached. A clamp is used to close the tube. Normally there are two spaced apertures which extend through the flap at the top edge of the bag. The apertures facilitate hanging of the bag on a holder.

Various means have been previously proposed for holding a plastic blood bag in a centrifuge. For example, a cylindrical cup-shaped member has been proposed in which the blood bag is simply inserted into the cup in a manner such that the top of the bag is at the top of the cup. However, the cup-shaped member does not include any means to assure that the top of the bag will not become folded during centrifuging and thereby entrap a portion of the whole blood. Also, any folds in the bag itself can entrap portions of the whole blood. As a result, the red blood cells in the trapped portions of the whole blood are prevented from becoming separated from the plasma during centrifuging since when the bag is removed from the centrifuge the trapped portions of the blood are freed and become mixed with the plasma. However, unless essentially all of the red blood cells are separated from the plasma, the plasma is medically unacceptable.

Although it has also been proposed to use an oval-shaped cup to hold the bag in the centrifuge so as to reduce the possibility of the blood bag rupturing during centrifuging. However, the use of such a holder increases the difficulty of removing the blood bag from the holder after centrifuging. As a result, disturbance of the red blood cells can occur, causing intermixing of red blood cells and plasma To overcome some of the foregoing problems there has been proposed a blood bag port support comprising a metal stand having a circular base section and an upper portion which includes two hooks to engage the upper edge of the blood bag while the blood bag is in the cup holder in a centrifuge. This type of port support, however, is unbalanced since it is asymmetrical. As a result, the centrifuge cup tips because of the heavier weight on one side of the cup. Thus, the bag is not aligned with the centrifugal force. Consequently, mixing or vortexing within the blood bag during centrifuging can occur, which results in red blood cells mixing with the plasma, and the plasma is not sufficiently platelet-rich. Yet another disadvantage of this type of holder is that the contents of the blood bag maybe disturbed when the bag is disconnected from the hooks of the holder after centrifuging, thus causing red blood cells to mix with the plasma. Also, different holders may be required for different types of bags.

Yet another type of blood bag holder is described in U.S. Pat. No. 3,830,425 which comprises a U-shaped member made of spring steel. The free ends of the U are adapted to be drawn together to secure the mouth of a blood bag which has been inerted therein. Clamps are then applied to the free ends to hold them tightly together. The holder, with the bag securely clamped in place, is then inserted into the centrifuge. However, this type of holder cannot be used with existing centrifuge cups; consequently, special cups must be used. Also, removal of the blood bag from the holder after centrifuging may be difficult to do without mixing of the red blood cells with the plasma. First the clamp must be loosened and removed, then the jaws must be spread and, while the jaws are held apart, the bag must be disengaged from the jaws and slid outwardly in a sideways motion. The greater the manipulation of the bag the greater is the chance of mixing the interface of the red blood cells and the plasma. With the advent of pilot bags containing nutritive additives, it would be necessary to have a larger cup and holder to serve the original purpose. Nutritive additives in pilot bags increase the total volume of the blood bag conglomeration by nearly 25%. This larger volume could not easily be accommodated, if at all, by the original holder-cup arrangement. Furthermore, different holders would be necessary for different types of blood bags.

There has not heretofore been provided a blood bag support system having the advantages inherent in the system of the present invention.

SUMMARY OF THE PRESENT INVENTION

In accordance with the present invention there is provided a blood bag support system which is adapted to support a blood bag of the type having at least two apertures at the top edge of the bag. The support system of the invention comprises:

(a) two spaced-apart, parallel upright support members, each of which has an upper end and a lower end on which the support member is adapted to rest; and (b) horizontally disposed connecting means extending between and engaging the upper ends of the upright support members.

The connecting means is adapted to extend through the apertures at the top edge of the blood bag and to support the blood bag between the two upright members, e.g., during centrifuging. The connecting means is adapted to be disconnected from the apertures of the blood bag after centrifuging the blood, if desired.

Alternatively, in one embodiment of the invention, one of the upright support members is removed (after centrifuging) while the blood bag is suspended from the connecting means attached to the other upright support member. Then the blood bag may be suspended in a plasma expressor extractor where the plasma is squeezed out of the bag through one or more ports at the top of the bag.

The blood bag support system of this invention is particularly desirable for several reasons. It is equally weighted on each side so that there is no mixing or vortexing within the blood bag during centrifuging. The support system also is adaptable to various sizes and types of blood bags (e.g., the support system can also accommodate pilot bags or satellite bags which may be attached to the blood bag). Such pilot bags may contain conventional additives such as Adsol ®, Nutricell ®, etc. which are added to the red blood cells after separation.

The support system is inexpensive, easy to use reliably, and allows for quick connecting and disconnecting of a blood bag, without risk of harm to the bag or its contents when used according to protocol. Furthermore, the support system can be used in any conventional centrifuge cup or holder. The support system may also be easily cleaned, if necessary, using antiseptic soap.

Moreover, another very important advantage of the support system of this invention is that no portion of the whole blood is trapped at the top of the bag during the centrifuging process because the support system prevents the tubes at the top of the bag from folding over and trapping blood. Accordingly, using the support system of this invention a very pure plasma is obtained which is red blood cell poor, i.e., essentially free of red blood cells. Previously available blood bag holders have not been able to consistently provide high purity plasma during centrifuging.

Another distinct advantage of the support system of the invention is that it may be used to support the blood bag in a plasma expressor after centrifuging the blood. To do this, one of the upright support members is detached while the other support member is slipped into a holder attached to one plate of the expressor, in a manner such that the blood bag is suspended between the two plates of the expressor apparatus. This technique avoids the need to transfer the blood bag from the support system to the prongs on the expressor. The conventional technique sometimes results in disturbance of the contents of the blood bag, with resulting undesirable mixing of a portion of the red blood cells with the plasma.

The support system of this invention is easy to disassemble, making it easier to remove the blood bag from the connecting means, if desired, without disturbing the interface between the red blood cells and the plasma. It is also easy to load the support system into a centrifuge cup with the blood bag attached. The support system also holds the sides of the bags taut to prevent formation of creases which might trap blood. The support system is also relatively inexpensive to produce.

Yet another advantage of the support system of this invention is that its use results in the reliable and efficient production of platelet-rich plasma which is void of red blood cells. The plasma can be obtained at a wider variety of spin times and centrifugal forces than is possible with the use of the metal stand device described above.

Other advantages of the system of this invention will be apparent from the following detailed description.

BRIEF DESCRIPTION OF THE DRAWINGS

The invention is described in more detail hereinafter with reference to the accompanying drawings, wherein like reference to the accompanying drawings, wherein like reference characters refer to the same parts throughout the several views and in which:

FIG. 1 is an isometric view of one embodiment of blood bag support system of the invention;

FIG. 2 is a top view of the support system of FIG. 1 illustrating the manner in which it is separated to allow connection to a blood bag;

FIG. 3 is a side elevational view illustrating one manner in which the support system of the invention can be used to support a blood bag in a plasma expressor;

FIG. 4 is a front elevational view showing a blood bag supported by the support system of the invention;

DETAILED DESCRIPTION OF THE INVENTION

Figure 5:
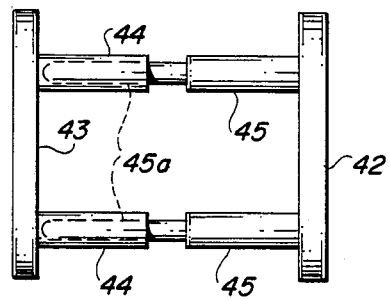
FIG. 5 is a top view of another embodiment of support system of the invention.

In FIG. 1 there is shown an isometric view of a preferred form of blood bag support system 10 of the invention. This support system includes upright support members 12 and 13 which are spaced-apart and parallel. The upper ends of the support members 12 and 13 are connected by means of connecting means comprising spaced-apart, parallel rod members 15 and 16 which extend horizontally between the upright members for the purpose of supporting a blood bag between the upright members.

Preferably upright support members 12 and 13 are of equal size and weight so that a blood bag suspended between them will not tilt, shake or otherwise cause disturbance of the contents when the entire assembly is in a spinning centrifuge to separate plasma from red blood cells. In other words, the upright support system is balanced so that there is equal weight on each side of a blood bag suspended from the connecting means.

The dimensions of the upright support members are not critical so long as the support system is capable of supporting a filled blood bag between the upright support members, and so long as the entire assembly can be placed in a cup or other holder in a conventional centrifuge. Typically, the height of each upright support member is in the range of about 5.75 to 6.2 inches so that the support system will fit easily within a conventional centrifuge without scraping the cover during centrifuging. The width of each upright support member is typically in the range of about 1.75 to 2 inches. The thickness of each upright support member may also vary, but typically it is in the range of about 0.2 to 0.3 inch.

The upright support members may be composed of a variety of materials. For example, they may be made of plastic (e.g., an impact-resistant, durable plastic such as polycarbonate, e.g., Tuffak ®, or other suitable plastic), metal (e.g., aluminum, stainless steel), wood or combinations of materials (e.g., metal which has been coated with plastic, or laminations of various materials). Preferably the support member are of approximately equal size and weight. The edges of the support members are rounded or bevelled to avoid sharp edges.

The connecting means which extend between the two upright members typically comprises two spaced-apart, parallel rod members which are capable of extending through apertures at the top edge of a blood bag and thereby support or suspend the blood bag between the two upright support members 12 and 13. In the embodiment illustrated in FIGS. 1 and 2 there is one pair of rod members 15a and 16a, each of which is secured to the upper end of upright support member 12, as illustrated. Secured to the upper end of the other upright support member 13 is a pair of elongated tubular members 15b and 16b which are spaced-apart and parallel. The diameter of tubular members 15b and 16b is such that the free ends of rod members 15a and 16a may be slidably received in tubular members 15b and 16b, respectively. In the embodiment shown in FIG. 1, the rod members 15a and 16a each comprise a short length of tubing in which one end of a solid rod is secured (e.g., by soldering or welding). The length of the exposed portion of each such solid rod is sufficient to extend into tubular members 15b and 16b as shown and illustrated. The diameter of the rods may be, for example, 3/16 inch, while the inside diameter of the tubes is 7/32 inch.

If desired, there may be affixed to the connecting means one or more stop members 17 which are preferably larger in diameter than the diameter of the apertures in the top edge of the blood bag. The stop members serve to retain the blood bag centered between the upright support members. The stop members may be composed of any desired material. For example, they may be sections of rubber tubing which are slipped onto the rod members and tubular members and retained in place by friction.

The connecting means may take forms other than the embodiments shown in FIGS. 1 and 2 so long as the connecting means is adapted to support the blood bag between the upright supports during centrifuging and so long as the blood bag may be attached and detached from the connecting means. In the embodiment illustrated in FIGS. 1 and 2 the connecting means comprises a multi-piece arrangement which enables the connecting means to be separated (as illustrated) so that the rod members may be extended through the apertures in the top edge of the blood bag and then slidably received in the tubular members carried by the other upright support member. This is a convenient and simple arrangement which is quite effective. Other arrangements are described hereinafter.

The diameter and cross-sectional shape of the rods and tubes of the connecting means may vary so long as the connecting means may be fitted through the apertures at the top edge of a blood bag. Generally the apertures have a diameter of about 3/32 to ⅛ inch. The diameter of the portion of the connecting means which is to extend through such apertures preferably is slightly greater than that so that the aperture is stretched slightly when the connecting means extends through it. It is preferred for the connecting means to have a diameter of at least about 0.1 to 0.2 inch. The cross-sectional shape of the connecting means is preferably circular or at least rounded at the top edge.

As illustrated in FIGS. 2 and 4, a conventional blood bag 20 has a top edge portion 25 which includes apertures 24 therethrough. It is through these apertures that the connecting means extends and supports the bag. The bag may include one or more ports 21, 22 and 23 which communicate with compartments in the bag. When desired, plasma may be expressed through ports 21, 22 or 23. For example, the plasma may be removed through port 22 and attached tube 22a by disconnecting a clamp member on tube 22. Alternatively, in some plastic blood bags the port 22 is sealed and is adapted to be opened by twisting or bending the port to break the seal. Ports 21 and 23 are accessible by piercing through flaps 21a and 23a, respectively, with a conventional spiked end transfer tube.

The types of blood bags with which the support system of the invention is useful may vary. Generally speaking, the support system may be used in conjunction with any blood bag having apertures at the top edge thereof and vertical port openings, as illustrated. Typically such blood bags have a capacity of about 450 cc. and are made of durable plastic. They are available commercially under various brand names such as FENWAL, DELMED, TERUMO, or CUTTER.

Preferably the blood bag is supported primarily by the connecting means and the upright supports while in the centrifuge. If the top edge portion 25 of the blood bag 20 is sufficiently tear-resistant, the entire weight of the filled bag may be supported from the connecting means during centrifuging. Typically, however, it is preferred for the base of the filled bag to be partially supported in the cup during the centrifuging process. For example, about one-fourth of the weight of the filled bag may be supported directly by the cup during centrifuging.

After the blood has been centrifuged using the support system of this invention, a preferred technique for removing the plasma and separating it from the red blood cells is illustrated in FIG. 3. The plasma expressor extractor is shown in a side elevational view and comprises a base member 30, an upright stationary plate member 32, and movable plate member 34 which is hinged at its lower edge 35. Plate member 34 may be pivoted in the direction of the arrow by means of lever or arm 36 from the outward position shown in FIG. 3 to an inward position at which it is parallel and adjacent to stationary plate 32.

The holder or plasma expressor adaptor 38 is secured to the rear surface of the stationary plate member 32. The holder may include a slotted aperture, for example, into which one of the upright supports 12 may be slidably received in order to suspend the blood bag 20 between the stationary plate 32 and the movable plate 34. This technique enables the blood bag to be removed from the centrifuge and then transferred to the plasma expressor apparatus without removing the bag from the connecting rods 15 and 16. All that is necessary is to detach one of the upright support members (e.g., member 13). As a result, there is much less disturbance of the bag than is typically associated with the conventional technique in which the blood bag mus be removed from the blood bag holder and then attached to prongs projecting outwardly from the stationary plate.

In order to separate the plasma from the red blood cells (which have been forced toward the bottom of the bag during centrifuging), the break-away seal or clamp at port 22 is opened to permit transfer of plasma to a satellite bag. Then movable plate 34 is urged towards stationary plate 32 so as to squeeze the bag slowly. As a result, plasma is expressly outwardly through port 22 and into tube 22a.

In FIG. 5 there is illustrated a top view of another embodiment of connecting means in which a pair of tubes 45 is secured at one end to one upright support member 42 in spaced-apart, parallel arrangement. Another pair of tubular members 44 is secured to the other upright support member 43 in spaced-apart, parallel fashion in a manner such that the rod members 45a secured to tubes 45 will be slidably received in tube members 44. Preferably the rod members 45a are longer than the length of tubular members 44 so that there is a section approximately mid-way between the two upright supports in which the top edge of the blood bag may rest when being held by the support system. The two upright support members are easily separated, when desired, in order to remove the blood bag again.

Figure 6:
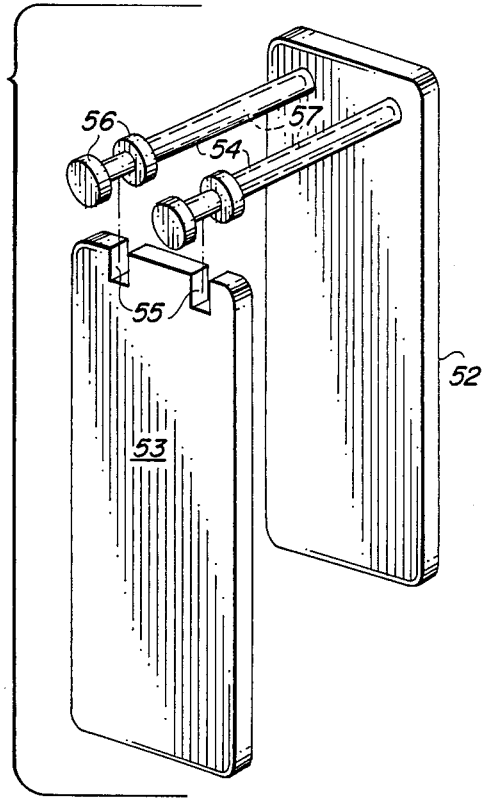
FIG. 6 is an isometric view of another embodiment of support system of the invention.

In FIG. 6 there is illustrated yet another embodiment of support system in which two tube members 54 are secured at one end to the upper portion of upright support member 52, as shown. The top edge of the other upright support member 53 includes two slots 55 which are adapted to receive the outer ends of two rod members 57 which are slidably received in tubes 54. Retainers 56 on the ends of the rod members 57 are adapted to be positioned on each side of support member 53 to assist in preventing the rod members from becoming disengaged from support member 53. When it is desired to place a blood bag onto the tubular members 54 it is only necessary to slide out rod members 57 and then replaced them again after the bag has been attached to tubes 4. The reverse process is used to detach the blood bag.

Figure 7:
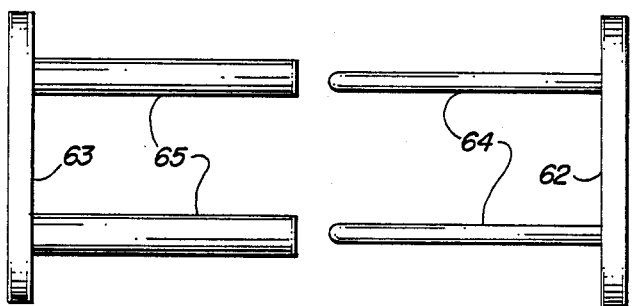
FIG. 7 is a top view of an alternative embodiment of support system of the invention.

FIG. 7 is a top view another embodiment of support system of this invention. In this embodiment a pair of elongated, spaced-apart rod members 64 are secured at one end to upright support member 62. A pair of elongated, spaced-apart tubular members 65 are secured at one end to the other upright support member 63, as shown. The free ends of rod members 64 are adapted to be slidably received in tubular members 65. The length of rod members 64 is approximately equal to the length of tubular members 65.

Figure 8:
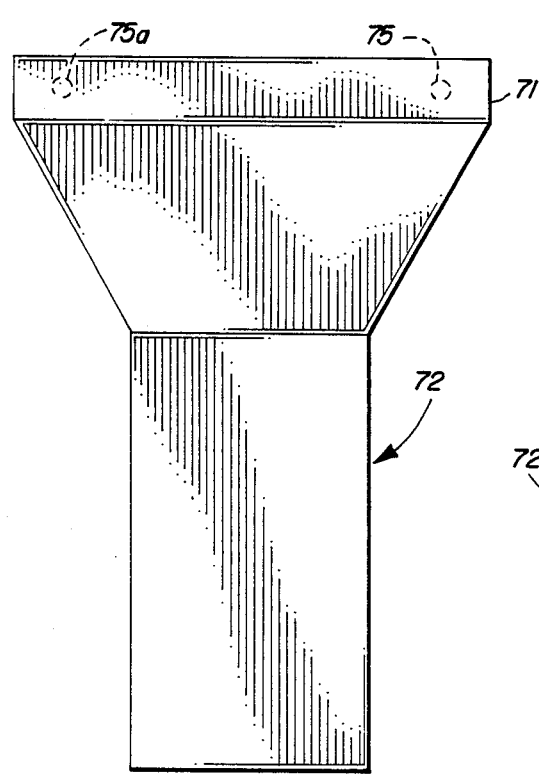
FIG. 8 is a front elevational view of another embodiment of support system of the invention.
Figure 9:
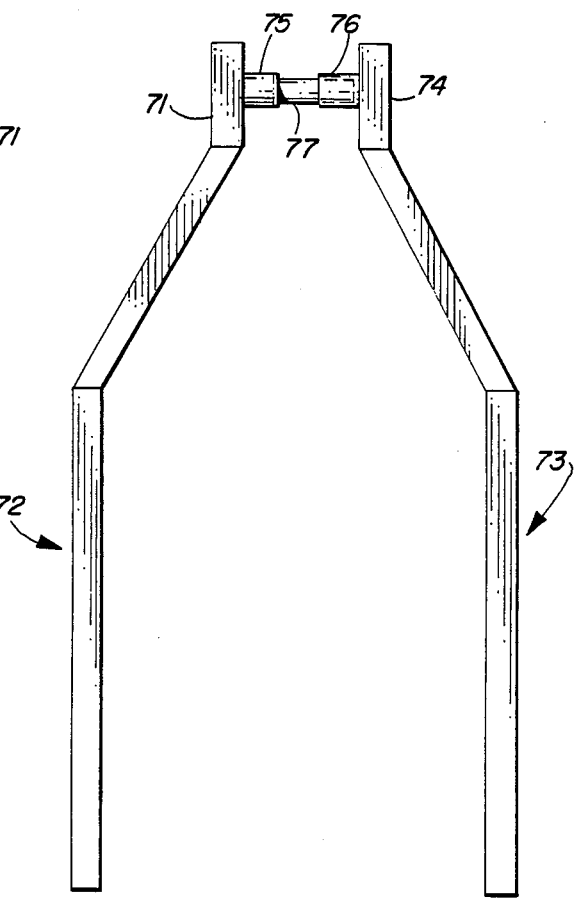
FIG. 9 is a side elevational view of the embodiment of support system shown in FIG. 8.

FIGS. 8 and 9 illustrate another embodiment of support system of this invention. In this embodiment, as shown in the side elevational view of FIG. 8, the upper end 71 of the support member 72 is wider than the base portion. As shown in FIG. 9, the upper ends 71 and 74 of the upright support members 72 and 73 are much closer together than are the base portions of the upright members.

Tubular members 75 and 75a are supported at one end to the upper portion 71 of the upright support member 72. Tubular members 76 are supported at one end to the upper portion 74 of the upright support member 73. A rod member 77 is secured to each of the tubular members 75 and 75a. The free end of each rod 77 is adapted to be slidably received in a tubular member 76, as illustrated.

To support a blood bag in this embodiment of support system, upright member 72 is detached by moving it laterally away from support member 73 until each rod 77 is free from each tube 76. Then a blood bag may be supported on the rods 77 and the upright members can again be moved together, as shown.

The embodiment of support system shown in FIGS. 8 and 9 is useful, for example, with blood bags in which the apertures at the top edge of the bag are widely spaced apart. The lower portions of the upright supports are narrower than the upper portions so that they will fit into the cup of a conventional centrifuge.

Other variations are also possible without departing from the scope of the present invention. For example, the lower portions of the upright members may have a greater thickness than the upper portions thereof. If desired, the base section of each upright member may include a fillet to protect against stretching of the bag during centrifuging. Of course, such a fillet would not serve any useful purpose if a satellite bag or transfer is attached to the blood bag.

What is claimed is:

1. A method for separating plasma from red blood cells of whole blood contained in a blood bag of the type having (i) at least one port at the top thereof which communicates with the interior of the blood bag, and (ii) at least two apertures at the top edge of the blood bag; wherein said method comprising the steps of:
    (a) providing a blood bag suport system having upright support members interconnected at their upper end by connectign means;
    (b) supporting the blood bag between the upright support members by extending the connecting means through the apertures at the top of the blood bag;
    (c) placing the support system and the blood bag in a centrifuge;
    (d) centrifuging the blood in the blood bag for a time sufficient to urge the red blood cells to the lower end of the blood bag;
    (e) removing the support system and the blood bag from the centrifuge;
    (f) detaching one of the upright support members;
    (g) placing the blood bag in a plasma expressor to support the blood bag from the connecting means; and
    (h) expressing the plasma from the blood bag through the port.

2. The method as set forth in claim 1 wherein the plasma expressor comprises an upright, stationary plate member and a press plate, the press plate being hinged at its lower edge and being movable between a first position tilted away from the stationary plate and a seocnd position parallel to the stationary plate.

3. A method for separating plasma from red blood cells of whole blood contained in a blood bag of the type having (i) at least one port at the top thereof which communicates with the interior of the blood bag, and (ii) at least two apertures at the top edge of the blood bag, wherein said method comprises the steps of:
    (a) providing a blood bag support system having upright support members interconnected at their upper end by connecting means the connecting means comprising;
        (i) a pair of spaced-apart, parallel rod members, each of the rod members being attached at one of its ends to the upper end of a first one of the upright support members, and
        (ii) a pair of spaced apart, parallel tubular members, each of the tubular members being attached at one of its ends to the upepr end of the second one of the upright support members, the free ends of the pair of rod members being slidably receivable within the pair of tubular members;
    (b) supporting the blood bag between the upright support members by extending the connecting means through the apertures at the top of the blood bag;
    (c) placing the support system and the blood bag in a centrifuge;
    (d) centrifuging the blood in the blood bag for a time sufficient to urge the red blood cells to the lower end of the blood bag;
    (e) removing the support system and the blood bag from the centrifuge;
    (f) detaching one of the upright support members;

(g) placing the blood bag in a plasma expressor to support the blood bag from the connecting means; and (h) expressing the plasma from the blood bag through the port.

4. The method as set forth in claim 3 wherein the blood bag is supported by the pair of parallel rod members in the plasma expressor.

5. The method as set forth in claim 3 further comprising holding means secured to the plasma expressor for receiving one of the upright support members and holding the blood bag in suspension between the stationary plate and the press plate.

6. The method as set forth in claim 5 wherein the holding means is attached to the rear surface of the statioanry plate and wherein the holding means includes a slotted opening for receiving one of the upright support members.

7. A blood bag support system for supporting a blood bag of the type having at least two apertures at the top edge of the blood bag, said support system comprising in combination;

(a) two spaced-apart, parallel, upright support members, each of said support members having an upper end and a lower end; and (b) horizontally disposed connecting means extending between and engaging the upper ends of said upright support members for penetrably engaging the apetures at the top edge of the blood bag, said connecting means comprising (i) a pair of spaced-apart parallel rod members, each of said rod members having one of its ends attached to the upper end of one of said upright support members, and (ii) a pair of spaced-apart parallel tubular members, each of said tubular members having one of its ends attached to the upper end of the other of said upright support members, the free end of each rod member of said pair of rod members being slidably receivable within a corresponding free end of a tubular member of said pair of tubular members;

whereby, said support system supports the blood bag between said upright support members from said connecting means.

8. The blood bag support system as set forth in claim 7 further comprising a first stop member carried by each rod member of said pair of rod members and a second stop member carried by each tubular member of said pair of tubular members for retaining the blood bag between said first and second stop members upon penetrable engagement of the apetures with said connecting means.

9. A blood bag support system particularly configured for supporting within a conventional blood centrifuge cup a blood bag of the type having at least two apertures at the top edge of the blood bag, said support system comprising in combination:

two spaced-apart, opposed support members, each of said support members being adapted to rest upon diametrically opposed locations of the centrifuge cup; and (b) horizontally disposed connecting means extending between and engaging said support members for penetrably engaging the apertures at the top edge of the blood bag, said connecting means comprising:

(i) a pair of spaced-apart parallel rod members, each of said rod members having one of its ends attached to one of said support members, and (ii) a pair of spaced-apart parallel tubular members, each of said tubular members having one of its ends attached to the other of said support members, the free end of each rod member of said pair of rod members being slidably receivable within a corresponding free end of tubular member of said pair of tubular members;

whereby, said support system supports the blood bag between said support members from said connecting means.

10. The blood bag support system as set forth in claim 9 further comprising a first stop member carried by each rod member of said pair of rod members and a second stop member carried by each tubular member of said pair of tubular members for retaining the blood between said first and second stop members upon penetrable engagement of the apertures with said connecting means.

* * * * *